US010525092B2

(12) United States Patent
Lefevre et al.

(10) Patent No.: US 10,525,092 B2
(45) Date of Patent: Jan. 7, 2020

(54) COMPOSITIONS AND METHODS FOR PREVENTING INFECTIONS

(71) Applicant: BIOCODEX, Gentilly (FR)

(72) Inventors: Jean-Marie Lefevre, Paris (FR); Gilles Renaud, Courbevoie (FR); Marie-Emmanuelle Le Guern, Compiegne (FR)

(73) Assignee: BIOCODEX, Gentilly (FR)

( * ) Notice: Subject to any disclaimer, the term of this patent is extended or adjusted under 35 U.S.C. 154(b) by 0 days.

(21) Appl. No.: 15/317,603

(22) PCT Filed: Jun. 11, 2015

(86) PCT No.: PCT/EP2015/063077
§ 371 (c)(1),
(2) Date: Dec. 9, 2016

(87) PCT Pub. No.: WO2015/189337
PCT Pub. Date: Dec. 17, 2015

(65) Prior Publication Data
US 2018/0153947 A1   Jun. 7, 2018

(30) Foreign Application Priority Data
Jun. 11, 2014   (EP) .................................... 14290168

(51) Int. Cl.
| | | |
|---|---|---|
| *A61K 9/19* | (2006.01) | |
| *A61K 47/12* | (2006.01) | |
| *A61K 47/26* | (2006.01) | |
| *A61P 1/12* | (2006.01) | |
| *A23L 33/14* | (2016.01) | |
| *A61K 36/064* | (2006.01) | |
| *A61J 1/20* | (2006.01) | |
| *A61J 7/00* | (2006.01) | |
| *A23P 10/40* | (2016.01) | |
| *A23L 33/15* | (2016.01) | |
| *A23L 33/16* | (2016.01) | |
| *A23L 33/125* | (2016.01) | |
| *A23L 33/155* | (2016.01) | |

(52) U.S. Cl.
CPC .......... *A61K 36/064* (2013.01); *A23L 33/125* (2016.08); *A23L 33/14* (2016.08); *A23L 33/15* (2016.08); *A23L 33/155* (2016.08); *A23L 33/16* (2016.08); *A23P 10/40* (2016.08); *A61J 1/2093* (2013.01); *A61J 7/0046* (2013.01); *A61K 9/19* (2013.01); *A61K 47/12* (2013.01); *A61K 47/26* (2013.01); *A61P 1/12* (2018.01); *A23V 2002/00* (2013.01)

(58) Field of Classification Search
CPC .............. A61K 31/192; A61K 2300/00; A61K 36/064; A61K 36/06; A61K 45/06; A61K 47/12; A61K 47/26; A61K 9/19
See application file for complete search history.

(56) References Cited

FOREIGN PATENT DOCUMENTS

| | | |
|---|---|---|
| CN | 202409492 U | 9/2012 |
| EP | 1852122 A1 | 11/2007 |
| JP | 1015035 A | 1/1998 |

OTHER PUBLICATIONS

Martins et al 2009 ,Archives of Microbiology, vol. 191, Issue 8, pp. 623-630 (Year: 2009).*
Anonymous,"Supplement Facts Florastor Kids—*Saccharomyces boulardii* lyon" http://www.florastor.com/probioticsupplements, pp. 1-6 (Jan. 2011).
M. Cassone et al.,"Outbreak of *Saccharomyces cerevisiae* Subtype *boulardii* Fungemia in Patients Neighboring Those Treated with a Probiotic Preparation of the Organism",Journal of Clinical Microbiology, pp. 5340-5343, vol. 41, No. 11 (Nov. 2003).
C. Hennequin et al., "Possible Role of Catheters in *Saccharomyces boulardii* Fungemia", European Journal of Clinical Microbiology & Infectious Diseases, pp. 16-20, vol. 19, No. 1 (Feb. 2000).
Yvan Vandenplas et al., "*Saccharomyces boulardi i* in childhood", European Journal of Pediatrics, pp. 253-265, vol. 168, No. 3 (Dec. 2008).
Database WPI,"Dual-chamber-type antibiotic medicine containing glass bottle. has bottle body provided with liquid medicine chamber and powder chamber. and connecting rod connected with bottle opening plug", (Sep. 2012).
Database WPI, "Nutrient liquid agent packed in container having chambers—with chamber containing powder of sugars. amino acids. electrolytes. fats and/or vitamin(s) and chamber containing", (Jan. 1998).
Lynne V McFarland,"Systematic review and meta-analysis of *Saccharomyces boulardii* in adult patients", World Journal of Gastroenterology, pp. 2202, vol. 16, No. 18 (Jan. 2010).

* cited by examiner

*Primary Examiner* — Padmavathi Baskar
(74) *Attorney, Agent, or Firm* — Browdy and Neimark, PLLC

(57) ABSTRACT

The present invention relates to a dietary supplement or pharmaceutical composition, comprising lyophylized *Saccharomyces boulardii* as an active ingredient and as sole probiotic, optionally in association with a pharmaceutically acceptable vehicle, wherein the composition is in a closed vial a having a first airtight compartment comprising lyophilized *S. boulardii* powder, and a second compartment comprising a solution, wherein the first and second compartment can be brought in airtight communication with one another to yield a suspension of *S. boulardii* to be administered to an individual upon opening of the vial.

6 Claims, 1 Drawing Sheet

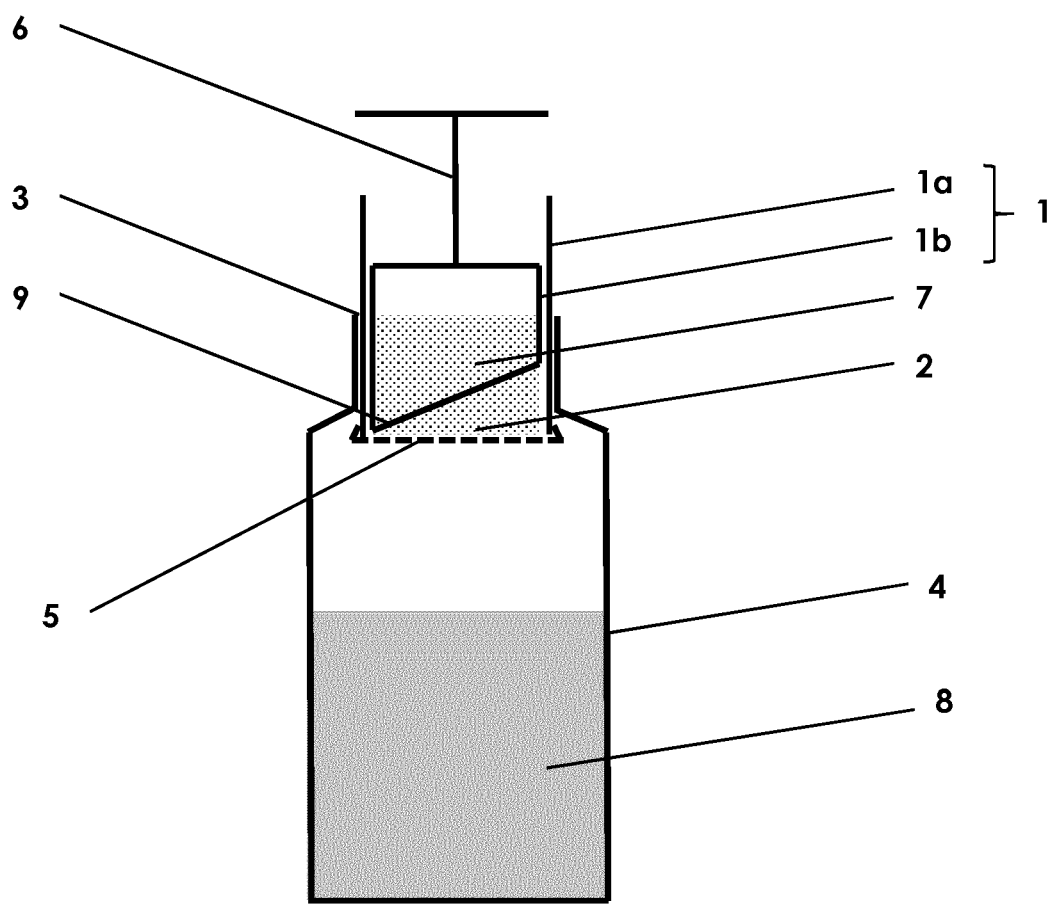

COMPOSITIONS AND METHODS FOR PREVENTING INFECTIONS

OBJECT OF THE INVENTION

The present invention relates to compositions and methods useful for preventing undesirable effects occasionally reported with *Saccharomyces boulardii* administration to individuals in need thereof.

TECHNICAL BACKGROUND

*Saccharomyces boulardii* is a particular strain of the yeast *Saccharomyces cerevisiae*, also referred to as *Saccharomyces cerevisae* var. *boulardii*, which is mainly indicated as a supplement to rehydration for the treatment of diarrhea.

Its usefulness has notably been established in the treatment of acute diarrhea due to infection in children and adults (Villarruel et al. (2007) *Acta Paediatr* 96:538-541; Szajewska et al. (2007) *Aliment Pharmacol Ther* 25:257-264), in the prevention of antibiotic-associated diarrhea in children and adults (Surawicz et al. (1989) *Gastroenterology* 96:981-988; Kotowska et al. (2005) *Aliment Pharmacol Ther* 21:583-590), in the prevention of *Clostridium difficile* diarrhea and colitis (Surawicz et al. (2000) *Clin Infect Dis* 31:1012-1017), in the prophylaxis of traveler's diarrhea (McFarland (2007) *Travel Med Infect Dis* 5:97-105), as well as in the prophylaxis of diarrhea in tube-fed patients (Schlotterer et al. (1987) *Nutrition Clinique et Métabolisme* 1:31-34; Bleichner et al. (1997) *Intensive Care Medicine* 23:517-523). Besides, *S. boulardii* has also been reported to be useful for managing irritable bowel syndrome (IBS) and inflammatory bowel diseases (IBD).

Safety and adverse event data collected during clinical trials, when patients are closely monitored for adverse effects possibly related to the investigational treatment, has documented a remarkable safety profile of *S. boulardii*. However, infrequent cases of *S. boulardii* fungemia have been occasionally reported, essentially in individuals which have central venous catheters. As such, it has sometimes been recommended not to give *S. boulardii* to immunocompromised patients or those with central catheters to reduce this risk (McFarland (2010) *World J Gastroenterol* 16:2202-2222; Santino et al. (2014) *Int J Immunopathol Pharmacol* 27:143-6).

However, these individuals could benefit from *S. boulardii* treatment, as it has notably been shown that *S. boulardii* was useful for managing pathologies such as HIV-associated diarrhea as well as enteral nutrition-related diarrhea that may arise in immunocompromised patients.

Accordingly, it is an object of the invention to reinforce the safety of *S. boulardii* usage by preventing undesirable effects.

SUMMARY OF THE INVENTION

The present invention arises from the recognition by the present inventors that these undesirable effects arise in part from the volatility of *Saccharomyces boulardii* powder, especially when lyophilized, which favors dissemination and opportunistic infections of this yeast, and from the finding that suspensions of lyophilized *S. boulardii* powder do not give rise to volatile dissemination of this yeast.

The present invention thus fulfills the above-defined objective by providing a dietary supplement or pharmaceutical composition, comprising lyophilized *Saccharomyces boulardii* as an active ingredient and preferably as sole probiotic, optionally in association with a pharmaceutically acceptable vehicle, wherein the composition is in a closed vial having a first airtight compartment comprising lyophilized *S. boulardii* powder and a second compartment comprising a solution, wherein the first and second compartment can be brought in airtight communication with one another to yield a suspension of *S. boulardii* to be administered to an individual upon opening of the vial.

As should be clear to one of skill in the art, the expression "wherein the composition is in a closed vial" indicates that the composition according to the invention is comprised in a closed vial. Accordingly, the present invention can be synonymously defined as a closed vial comprising a dietary supplement or pharmaceutical composition, wherein the composition comprises lyophilized *Saccharomyces boulardii* as an active ingredient, optionally in association with a pharmaceutically acceptable vehicle, and the closed vial has a first airtight compartment comprising lyophilized *S. boulardii* powder and a second compartment comprising a solution, wherein the first and second compartment can be brought in airtight communication with one another to yield a suspension of *S. boulardii* to be administered to an individual upon opening of the vial Alternatively, the invention can be further equivalently defined as a dietary or pharmaceutical product constituted of a dietary supplement or pharmaceutical composition, comprising lyophylized *Saccharomyces boulardii* as an active ingredient and preferably as sole probiotic, optionally in association with a pharmaceutically acceptable vehicle, comprised in a closed vial having a first airtight compartment comprising lyophilized *S. boulardii* powder and a second compartment comprising a solution, wherein the first and second compartment can be brought in airtight communication with one another to yield a suspension of *S. boulardii* to be administered to an individual upon opening of the vial.

In an embodiment of the invention, the dietary or pharmaceutical product, the dietary supplement or pharmaceutical composition as defined above, is for use for maintaining the balance of the intestinal flora, for keeping intestines functioning well, for maintaining normal bowel function, and/or for promoting intestinal health of the individual.

In another embodiment of the invention, the dietary or pharmaceutical product, the dietary supplement or pharmaceutical composition as defined above, is for use (i) in the prevention or treatment of microbial imbalance of the digestive tract, in particular for use in the prevention or treatment of diarrhea, such as antibiotic-associated diarrhea, Traveler's diarrhea, enteral-nutrition diarrhea, acute gastroenteritis in adult or children, HIV-related diarrhea, or giardiasis, more particularly for use as an additional symptomatic treatment of diarrhea in complement to rehydration, and/or (ii) in the prevention or treatment of bacterial, fungal or protozoan infection, such as *Clostridium difficile* infection, *Helicobacter pylori* infection, *Salmonella* infection, *Shigella* infection, *Cryptosporidium* infection, or oral candidiasis, and/or (iii) in the prevention or treatment of inflammatory bowel disease or irritable bowel syndrome, in the individual.

In another embodiment of the invention, the dietary or pharmaceutical product, the dietary supplement or pharmaceutical composition as defined above or for use as defined above, is for use in the prevention of *S. boulardii* fungemia.

In yet another embodiment of the invention, the dietary or pharmaceutical product, the dietary supplement or pharmaceutical composition as defined above or for use as defined above, is not for use in the dentistry field or in the treatment of diseases of the oral cavity, such as diseases of the oral mucosa, of the gums, and of the tooth-support tissues, and in particular is not for use for re-establishing eubiosis in gingivitis or periodontitis or for reducing halitosis.

The present invention further relates to a method for administering *S. boulardii* to an individual in need thereof and optionally to prevent *S. boulardii* fungemia in the individual, comprising:

providing a dietary supplement or pharmaceutical composition, comprising lyophylized *Saccharomyces boulardii* as an active ingredient and preferably as sole probiotic, optionally in association with a pharmaceutically acceptable vehicle, wherein the composition is in a closed vial having a first airtight compartment comprising lyophilized *S. boulardii* powder and a second compartment comprising a solution;

bringing the first and second compartment in airtight communication with one another to yield a suspension of *S. boulardii*;

administering the suspension to the individual.

The present invention also relates to a method for maintaining the balance of the intestinal flora, for keeping intestines functioning well, for maintaining normal bowel function, and/or for promoting intestinal health of an individual, comprising administering the individual an effective quantity of *Saccharomyces boulardii* with the above-defined method for administering *S. boulardii*.

The present invention also relates to a method for (i) the prevention or treatment of microbial imbalance of the digestive tract, in particular for the prevention or treatment of diarrhea, such as antibiotic-associated diarrhea, traveler's diarrhea, enteral-nutrition diarrhea, acute adult or children diarrhea, HIV-related diarrhea, or giardiasis, more particularly for use as an additional symptomatic treatment of diarrhea in complement of rehydration, and/or (ii) for the prevention or treatment of bacterial, fungal or protozoan infection, such as *Clostridium difficile* infection, *Helicobacter pylori* infection, *Salmonella* infection, *Shigella* infection *Cryptospordium* infection, or oral candidiasis, and/or (iii) in the prevention or treatment of inflammatory bowel disease or irritable bowel syndrome, in an individual, comprising administering the individual a prophylactically or therapeutically effective quantity of *S. boulardii* with the above-defined method for administering *S. boulardii*.

BRIEF DESCRIPTION OF THE DRAWING

FIG. 1 depicts a cross section of a vial according to the invention.

DETAILED DESCRIPTION OF THE INVENTION

*Saccharomyces boulardii*

*Saccharomyces boulardii*, abbreviated *S. boulardii*, is a yeast well known to a person skilled in the art and is notably described in Hennequin et al. (2001) *J. Clin. Microbiol.* 39:551-559. As intended herein "*Saccharomyces boulardii*" and "*Saccharomyces cerevisiae* var. *boulardii*" (abbreviated *S. cerevisiae* var. *boulardii*) are considered equivalent.

Preferably, *Saccharomyces boulardii* cells according to the invention are obtained from medicinal products of the brand Ultra-Levure®, Bioflor®, Codex®, Econorm®, Enflor®, Enteral®, Florastor®, Floratil®, Florestor®, Inteflora®, Perenterol®, Perenteryl®, Precosa®, Reflor®, or Ultra-Levura®. *Saccharomyces boulardii* cells according to the invention can also be obtained from deposits in the American Type Culture Collection (ATCC, USA) under reference 74012, in the *Collection Nationale de Culture et de Microorganismes* (CNCM, Institut Pasteur, France) under reference 1-745 or in the *Centraalbureau voor Schimmelcultures* (CBS, The Netherlands) under reference Hansen CBS 5926 strain.

The *S. boulardii* cells according to the invention are lyophilized.

Advantageously, the viability and vitality of *S. boulardii* cells obtained from lyophilizates are greater than can be obtained with other methods of preservation of yeast cells.

As understood here, "lyophilization", also known as freeze-drying, is a method of preservation in which *S. boulardii* live cells are frozen and are then submitted to sublimation of the frozen water that they contain to give a lyophilizate in the form of dry yeast powder preferably containing less than 2% of water and more preferably less than 1% of water. Preferably, the lyophilized yeast cells are obtained from concentrates of *S. boulardii* cells. Any type of method of lyophilization of yeast cells known by a person skilled in the art can be used. However, the *S. boulardii* cells are preferably lyophilized according to the invention by means of the following method of lyophilization:

cultivate the *S. boulardii* cells in a liquid nutrient medium until the cells reach a stationary phase;

concentrate the cultivated *S. boulardii* cells and freeze the concentrate, optionally in the presence of a cryoprotectant, such as lactose;

lyophilize the concentrate.

Lyophilized *S. boulardii* cells are in the form of a powder.

As intended herein, *S. boulardii* is preferably the sole probiotic comprised in the dietary supplement or pharmaceutical composition of the invention. In other words, no other probiotics, such as lactobacilli, are present in the dietary supplement or pharmaceutical composition of the invention in addition to *S. boulardii*. As defined by the Food and Agriculture Organization of the United Nations, a probiotic is a living (or revivable) microorganism, such as a bacteria or a yeast, which when administered in adequate amounts confer a health benefit to the host.

Individual

As intended herein, the individual is a mammal, preferably a human.

The individual may beneficiate from *S. boulardii* administration, i.e. may be in need thereof. Preferably, the individual is at risk of *S. boulardii* fungemia, such as an individual with a central venous catheter or an immunocompromised individual.

Besides, the volume of the solution as defined above may be minimized while ensuring complete suspension of the powder thereby facilitating administration to individuals such as babies or young children, or individuals with a deglutition disorder.

Vial

As intended herein "airtight" means that substantially no lyophilized *S. boulardii* powder can escape from the airtight first compartment and that substantially no water either liquid or gaseous can enter the airtight first compartment.

The second compartment is preferably also airtight.

As intended herein, when the first and second compartment are in airtight communication, the content of the first compartment can be mixed with the solution of the second compartment, while substantially no lyophilized *S. boulardii* powder can escape from the vial.

Upon mixing of the content of the first compartment and the solution of the second compartment to yield the suspension of *S. boulardii*, the closed vial can be opened so that the suspension can be administered.

Numerous configurations of the vial compatible with the invention can be devised by one of skill in the art.

In a preferred embodiment of the vial according to the invention, such as depicted in FIG. 1, the first compartment (1) has a single opening (2) which is fitted in an airtight manner (e.g. forced or screwed) in the single opening (3) of the second compartment (4), the opening (2) of the first compartment is shut by a removable airtight wall (5), and the vial comprise a means (6) for removing the airtight wall without opening the vial. Upon action of the means for removing the airtight wall, the content (7) of the first compartment (1) and the solution (8) can be mixed to yield a suspension and the first and second compartments can be separated (e.g. pulled or unscrewed) thereby opening the vial and yielding access to the suspension. By way of example, the means for removing the airtight wall (6) can be a cutting edge (9) set on an extremity of the first compartment facing the opening thereof (2) which can be motioned to cut the airtight wall (5), for instance by applying a translational force in direction of the second compartment, optionally combined with a rotational force. In the embodiment shown in FIG. 1, the first compartment (1) comprises two parts, a fixed part (1*a*) and a mobile part (1*b*), the mobile part holds the cutting edge (9) and closes the extremity of the first compartment (1) opposite to the opening (2) thereof while the fixed part is fitted in the single opening (3) of the second compartment (4). The mobile part (1*a*) is fitted in an airtight manner (e.g. forced or screwed) in the fixed part (1*b*) and can be motioned in direction of the second compartment (4).

The vial according to the invention can be made of various materials, such as glass and/or plastic. By way of example, the first compartment can be made of a plastic material while the second compartment can be made of glass. One of skill in the can easily select numerous materials which can be used for making the removable wall, such as aluminum foil.

Additional ingredients can be comprised in the first compartment, such as lactose and/or magnesium stearate, preferably in powder form.

When present, lactose is preferably at a dose of about 0.1 mg to 0.15 mg per mg of lyophilized *S. boulardii* powder, more preferably at a dose of about 0.132 mg per mg of lyophilized *S. boulardii* powder. According to the invention, lactose is useful as a cryoprotectant for freeze-drying of *S. boulardii*.

When present, magnesium stearate is preferably at a dose of about 0.005 mg to 0.015 mg per mg of lyophilized *S. boulardii* powder or per mg of a mixture of lyophilized *S. boulardii* powder and lactose, preferably with the above-defined dosage of lactose. According to the invention magnesium stearate is useful as an anti-adherent and a lubricant for filling the first compartment with lyophilized *S. boulardii* powder. Surprisingly, according to the invention, although magnesium stearate is known to be insoluble in water, its presence in the first compartment does not impair the mixing of the content of the first compartment and that of the second compartment to yield a suspension of *S. boulardii*.

The solution can have any constitution yielding a suspension of *S. boulardii* and compatible with administration by the oral route. Preferably, the solution comprises water, more preferably purified water. The solution may further comprise at least one of a sweetener, such as fructose, an aroma, such as red-fruit aroma, citric acid, and a preservative, such as potassium sorbate and sodium benzoate. Preferably, the suspension of *S. boulardii* according to the invention is not a mouth-wash liquid or a gel ready for topical use.

The dietary supplement or pharmaceutical composition according to the invention may further comprise at least one mineral, such as zinc or selenium, and/or at least one vitamin, such as vitamin A, either in the first compartment, preferably in powder form, or in the second compartment, preferably as a solute.

Form, Dosage and Administration

As intended herein, a dietary supplement composition is a non-medicament composition intended to improve the well-being of an individual through ingestion an active ingredient. As intended herein "dietary supplement" is considered equivalent to "nutraceutic".

As intended herein a pharmaceutical composition is a composition intended to restore the health of an individual and/or to prevent or treat a disease. Besides, a "pharmaceutical product" is considered synonymous to "medicament".

As intended herein the "active ingredient" is the causative agent of the beneficial, preventive or therapeutic effects of the composition of the invention.

The pharmaceutical composition may also comprise a pharmaceutically acceptable vehicle. As intended herein, a "pharmaceutically acceptable vehicle" relates to any compound or group of compounds compatible for administration to an individual without significant adverse effect intended to facilitate administration or action of the active ingredient.

Preferably, the first compartment comprises from 5 mg to 5 g, more preferably from 50 mg to 500 mg, most preferably about 250 mg of lyophilized *S. boulardii* powder.

Preferably the volume of the solution in the second compartment is from 0.5 mL to 10 mL, more preferable from 1 mL to 4 mL, most preferable about 2 mL.

Preferably, the suspension is at a concentration of from 10 mg of lyophilized *S. boulardii* powder per mL of solution to 1 g lyophilized *S. boulardii* powder per mL of solution, more preferably at a concentration of from 50 mg of lyophilized *S. boulardii* powder per mL of solution to 500 mg lyophilized *S. boulardii* powder per mL of solution, most preferably at a concentration of about 125 mg of lyophilized *S. boulardii* powder per mL of solution.

Preferably, the suspension of *Saccharomyces boulardii* obtained according to the invention is intended to be administered, or is administered, by the oral route.

Besides, the composition according to the invention may comprise a unit dose of *S. boulardii* or may comprise a dose of *S. boulardii* adapted for several administrations.

EXAMPLE

By way of example, a vial of the invention is as depicted in FIG. 1 and can have the following constitution:

The first compartment comprises 250 mg of lyophilized *S. boulardii* powder along with 32.5 mg lactose powder and 2.85 mg magnesium stearate.

The second compartment comprises a 2 mL solution of purified water and fructose, aroma, citric acid and preservatives (potassium sorbate, sodium benzoate).

The invention claimed is:

1. A method for administering *S. boulardii* to an individual for maintaining the balance of the intestinal flora of the individual, comprising: providing a dietary supplement or pharmaceutical composition, comprising lyophylized *Saccharomyces boulardii* as an active ingredient, optionally in association with a pharmaceutically acceptable vehicle, wherein the composition is in a closed vial having a first airtight compartment comprising lyophilized *S. boulardii* powder and magnesium stearate and/or lactose, and a second compartment comprising a solution and wherein the amount of lyophilized *S. boulardii* powder in the first compartment is in a range of 125 mg to 500 mg and the amount of magnesium stearate in the first compartment is 0.005 mg to 0.015 mg per mg of the lyophilized *S. boulardii* powder in the first compartment and/or the amount of lactose in the first compartment is in a range of 0.1 mg to 0.15 mg per mg of the lyophilized *S. boulardii* powder in the first compartment; bringing the first and second compartment in airtight communication with one another to yield a suspension of *S. boulardii*; administering the suspension to the individual.

2. The method of claim 1, for keeping intestines of the individual functioning well.

3. The method of claim 1, for maintaining normal bowel function of the individual.

4. The method of claim 1, for promoting intestinal health of the individual.

5. The method of claim 1, wherein, in the dietary supplement or pharmaceutical composition, the first compartment further comprises lactose.

6. The method of claim 1, wherein the dietary supplement or pharmaceutical composition further comprises at least one mineral and/or at least one vitamin.

* * * * *